United States Patent [19]

Tominaga et al.

[11] 4,210,753
[45] Jul. 1, 1980

[54] CARBOSTYRIL COMPOUNDS

[75] Inventors: Michiaki Tominaga; Hitoshi Tone; Kazuyuki Nakagawa, all of Tokushima, Japan

[73] Assignee: Otsuka Pharmaceutical Co., Ltd., Tokyo, Japan

[21] Appl. No.: 965,470

[22] Filed: Nov. 30, 1978

Related U.S. Application Data

[63] Continuation-in-part of Ser. No. 778,537, Mar. 17, 1977, abandoned.

[30] Foreign Application Priority Data

Mar. 17, 1976 [JP] Japan .................................. 51/28957
May 7, 1976 [JP] Japan .................................. 51/52498

[51] Int. Cl.² .......................................... C07D 413/12
[52] U.S. Cl. .................................. 544/128; 544/363; 546/157; 546/158; 424/248.54; 424/250; 424/258
[58] Field of Search ................ 544/363, 128; 546/157, 546/158

[56] References Cited

U.S. PATENT DOCUMENTS 4,072,683  2/1978  Nakagawa et al. .................. 424/258
4,147,869  4/1979  Nakagawa et al. .................. 544/363

Primary Examiner—Henry R. Jiles
Assistant Examiner—R. W. Ramsuer
Attorney, Agent, or Firm—Sughrue, Rothwell, Mion, Zinn and Macpeak

[57] ABSTRACT

Carbostyril compounds represented by the formula (I):

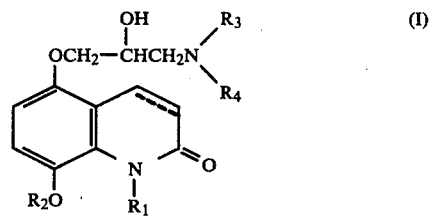

wherein $R_1$ represents a hydrogen atom, $R_2$ represents a hydrogen atom, a phenylalkyl group, an alkoxyalkyl group, a hydroxyalkyl group, an alkylcarbonyl group, an alkynyl group, $R_3$ and $R_4$ each represents a hydrogen atom, a heterocyclic alkyl group or $R_3$ and $R_4$ can form, when taken together with the nitrogen atom to which they are attached, a 5- or 6-membered heterocyclic ring which may contain a nitrogen atom or an oxygen atom as an additional hetero atom, the 3,4-bond of the carbostyril nucleus represents a single or double bond, pharmaceutically acceptable acid addition salts thereof, and process for preparing the same.

8 Claims, No Drawings

CARBOSTYRIL COMPOUNDS

CROSS-REFERENCE TO RELATED APPLICATION

This is a Continuation-in-Part Application of the Applicants' Application Ser. No. 778,537 filed Mar. 17, 1977, now abandoned.

BACKGROUND OF THE INVENTION

1. Field of the Invention

This invention relates to carbostyril derivatives and a process for preparing the same. More particularly, this invention relates to carbostyril derivatives represented by the formula (I) hereinafter described, the pharmaceutically acceptable acid addition salts thereof, and a process for preparing the carbostyril derivatives of the formula (I).

2. Description of the Prior Art

It is well known that certain carbostyril derivatives exhibit useful pharmaceutical activities. Representative compounds of this type have been disclosed in Journal of Medical Chemistry, Vol. 15, No. 3, pp. 260–266 (1972), Japanese Patent Publication No. 38789/1971 and Chemical Abstracts, 62, 16212e (1965), etc. However, these prior art references do not teach that the compounds having a wide variety of substituents at the 1-, 5- and/or 8-position of the carbostyril or 3,4-dihydrocarbostyril moiety possess an excellent β-adreno-receptor blocking activity.

Hitherto, various carbostyril compounds have been disclosed as having a β-adrenoreceptor blocking activity. For example, U.S. Pat. Nos. 3,340,266, 3,310,924 and 3,953,456, and German Patent Application DT No. 2,549,889 disclose that carbostyril or 3,4-dihydrocarbostyril derivatives having a (2-hydroxy-3-substituted-amino)propoxy group at the 5-, 6-, 7- or 8-position of the carbostyril or 3,4-dihydrocarbostyril nucleus possess a β-adrenoreceptor blocking activity.

However, these β-adrenoreceptor blocking agents, i.e., β-blockers, are usually contraindication to subject suffering from bronchial asthma and, therefore, it has been desired to develope β-blockers having a high cardioselectivity.

Recently, carbostyril compounds having a (2-hydroxy-3-substituted-amino)propoxy group at the 5-position of the carbostyril nucleus were found to have a cardioselective β-adrenoreceptor blocking activity, as disclosed in German Patent Application DT No. 2,615,406. Such cardioselective β-blockers would be very useful for treatment of cardiac disorders such as angina pectoris, heart arrhythmia and hypertension. The compounds of the present invention were also found to have excellent cardioselectivity better than that of these known compounds and are useful in treatment or prophylaxis of cardiac disorders in subjects suffering also from chronic obstructive lung disease such as bronchial asthma.

DETAILED DESCRIPTION OF THE INVENTION

As a result of extensive studies, it was found that the carbostyril derivatives having the formula (I) above and the pharmaceutically acceptable acid addition salts thereof possess an excellent cardioselective β-blocking activity.

The term "phenylalkyl" as used herein for $R_2$ means a monophenylalkyl or diphenylalkyl group having a straight or branched chain alkyl group having 1 to 6 carbon atoms in the alkyl moiety and includes, for example, a benzyl, 2-phenylethyl, 1-phenylethyl, 2-methyl-2-phenylpropyl, diphenylmethyl, 2,2-diphenylethyl, 4-phenylbutyl, 6-phenylhexyl, 1,1-dimethyl-2-phenylethyl, 2-methyl-4-phenylbutyl, 2-methyl-3-phenylpropyl group and the like.

The term "alkoxyalkyl" as used herein for $R_2$ means an alkoxyalkyl group having a straight or branched chain alkoxy group of 1 to 6 carbon atoms in the alkoxy moiety thereof and a straight or branched chain alkylene group of 1 to 6 carbon atoms in the alkyl moiety thereof and includes an ethoxymethyl, 2-methoxyethyl, 2-isopropoxyethyl, 3-butoxypropyl, 5-sec-butoxypentyl, 4-hexyloxybutyl, 6-pentyloxyhexyl, 3-ethoxybutyl and the like.

The term "hydroxyalkyl" as used herein for $R_2$ means a monohydroxyalkyl group having a straight or branched chain alkyl group of 1 to 6 carbon atoms and includes, for example, a hydroxymethyl, 2-hydroxyethyl, 3-hydroxypropyl, 2-hydroxypropyl, 4-hydroxybutyl, 3-hydroxybutyl, 2-methyl-3-hydroxypropyl, 5-hydroxypentyl, 4-hydroxypentyl, 2-methyl-4-hydroxybutyl, 2-methyl-3-hydroxybutyl, 6-hydroxyhexyl, 5-hydroxyhexyl, 2-methyl-5-hydroxypentyl, 2-methyl-4-hydroxypentyl group and the like.

The term "alkylcarbonyl" as used herein for $R_2$ means an alkylcarbonyl group having a straight or branched chain alkyl group of 1 to 6 carbon atoms in the alkyl moiety thereof and includes, for example, an acetyl, propionyl, butyryl, isobutyryl, pentanoyl, hexanoyl group and the like.

The term "alkynyl" as used herein for $R_2$ means a straight or branched chain alkynyl group having 2 to 7 carbon atoms and includes, for example, 2-propynyl, 1-propynyl, 2-butynyl, 3-butynyl, 2-pentynyl, 3-pentynyl, 4-pentynyl, 2-methyl-3-butynyl, 1-methyl-3-butynyl, 2-hexynyl, 3-hexynyl, 4-hexynyl, 5-hexynyl, 2-methyl-4-pentynyl, 1-methyl-4-pentynyl, 2-methyl-3-pentynyl, 1-methyl-3-pentynyl, 2-heptynyl, 3-heptynyl group and the like.

The term "heterocyclic alkyl" as used herein for $R_3$ and $R_4$ means a heterocyclic alkyl group consisting of a straight or branched alkylene group of 1 to 6 carbon atoms and a 5- or 6-membered heterocyclic ring containing at least one nitrogen atom and, optionally, an additional nitrogen atom and/or an oxygen atom, the alkylene group being attached to the nitrogen atom of the heterocyclic ring. Examples of the heterocyclic alkyl group are a pyrrolidinomethyl, 2-piperazinoethyl, 3-morpholinopropyl, 2-piperazinopropyl, 2-imidazolidinoethyl, 3-piperazinobutyl, 6-morpholinohexyl group and the like.

The term "5- or 6-membered heterocyclic ring" as used herein means heterocyclic groups containing at least one nitrogen atom and, optionally, an oxygen atom as hetero atoms such as piperidino, morpholino, pyrrolidino, piperazino, imidazolidino group and the like.

The above phenylalkyl and heterocyclic alkyl groups and the heterocyclic ring may contain 1 to 3 substituents which may be the same or different. Examples of such substituents include an alkyl group having 1 to 4 carbon atoms such as a methyl, ethyl, propyl, isopropyl, n-butyl, tert-butyl group and the like, an alkoxy group having 1 to 4 carbon atoms such as a methoxy, ethoxy, isopropoxy, n-butoxy, tert-butoxy group and the like, a halogen atom such as a chlorine, bromine, iodine or fluorine atom, an alkylenedioxy group having 1 to 2 carbon atoms such as a methylenedioxy or ethylenedioxy group and the like, a carbamoyl group, a substituted or unsubstituted phenyl group, etc.

Typical examples of groups having the above substituents are for example, 4-methoxyphenyl, 3-chlorophenyl, 3,4-methylenedioxy, 3,4-dimethoxyphenyl, 3,4,5-trimethoxyphenyl, 4-chlorophenyl, 2-(4-fluorophenyl)ethyl, 2-(3,4-dibromophenyl)ethyl, 2-(3,4-dimethoxyphenyl)ethyl, 2-(3,4,5-trimethoxyphenyl)ethyl, 4-(3,4,5-triethoxyphenyl)butyl, 2-(3,4-methylenedioxyphenyl)ethyl, 3-(3,5-dichlorophenyl)propyl, 2-(4-carbamoylphenyl)ethyl, 2-(4-chloro-3,5-dimethoxyphenyl)ethyl, 2-(2-isopropoxyphenyl)ethyl, 2-(3,4-dimethoxyphenoxy)ethyl, 2-(3,5-dimethoxyphenoxy)ethyl, 4-(3,4,5-triethoxyphenoxy)butyl, 2-(3,4-ethylenedioxyphenoxy)ethyl, 2-(4-fluorophenoxy)ethyl, 2-(4-tert-butoxyphenoxy)ethyl, 3-(3,5-dichlorophenoxy)propyl, 2-(4-carbamoylphenoxy)ethyl, 2-(4-chloro-3,5-dimethoxyphenoxy)ethyl, 2-(4-methoxyphenoxy)ethyl, 4-phenylpiperazino, 4-(4-methoxyphenyl)piperazino, 4-(3-chlorophenyl)piperazino, 4-(4-chlorophenyl)piperazino, 4-ethylpiperazino, 4-(tert-butyl)piperazino, 4-(2-methoxyphenyl)piperazino, 3-methyl-4-(4-chlorophenyl)piperazino, 3-isopropylpiperazino, 4-(3,4-methylenedioxyphenyl)piperazino, 2-chloropiperazino, 4-(3,4-dimethoxyphenyl)piperazino, 4-(2-methylphenyl)piperazino, 3-(4-ethylpiperazino)propyl, 2-(2-chloromorpholino)ethyl, 4-fluoropiperidino, 3-ethylpiperidino, 2-isopropylpyrrolidino and the like.

The term "pharmaceutically acceptable acid addition salts" as used herein means those formed with pharmaceutically acceptable inorganic and organic acids which are well known in the art such as, for example, hydrochloric acid, hydrobromic acid, hydroiodic acid, sulfuric acid, phosphoric acid, acetic acid, lactic acid, oxalic acid, malonic acid, succinic acid, maleic acid, fumaric acid, malic acid, mandelic acid, methanesulfonic acid, benzoic acid and the like.

The chemical structure representing carbostyril compounds of the present invention used throughout the specification and claims of this invention, i.e., the partial structure having the formula:

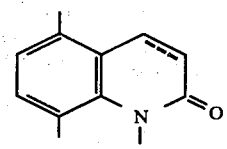

includes both carbostyril and 3,4-dihydrocarbostyril of the partial structure:

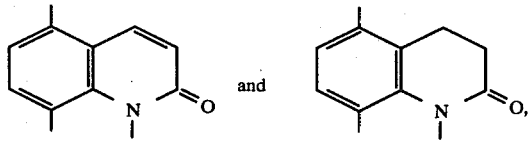

respectively.

The carbostyril derivatives represented by the formula (I) can be prepared by reacting a carbostyril compound of the formula (II), i.e., a 2,3-epoxypropoxycarbostyril compound of the formula (IIa) or a 2-hydroxy-3-halopropoxycarbostyril compound of the formula (IIb), with an amine compound of the formula (III), as illustrated by the following reaction scheme:

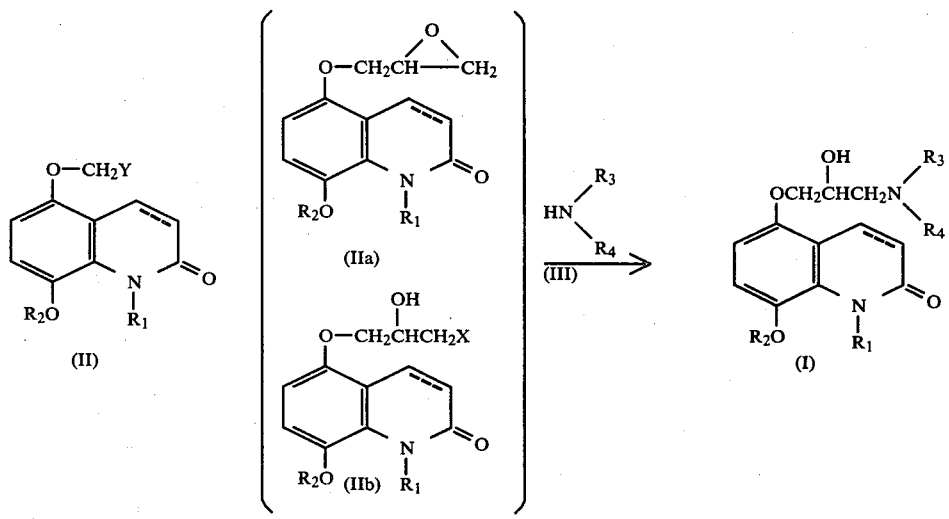

wherein $R^1$, $R^2$, $R^3$ and $R^4$ are as defined above, and Y represents

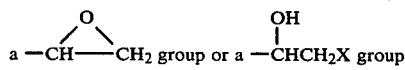

wherein X represents a halogen atom.

More specifically, the starting material, carbostyril compounds of the formula (II), can be either an epoxy form having the formula (IIa), a 2-hydroxy-3-halopropoxy form having the formula (IIb) or a mixture thereof.

The reaction between a 2,3-epoxypropoxycarbostyril compound of the formula (IIa) and an amine of the formula (III) can be carried out in the absence of solvents, but is preferably conducted in the presence of a solvent, for example, ethers such as dioxane, tetrahydrofuran and the like, aromatic hydrocarbons such as benzene, toluene, xylene and the like, water, dimethylformamide, etc., more preferably in a polar solvent such as methanol, ethanol, isopropanol and the like.

The reaction can be carried out at a temperature of about 0° C. to 100° C., preferably 0° C. to 70° C., using an approximately equimolar amount to a molar excess, preferably 3 to 8 mols, of the amine of the formula (III) per mol of the 2,3-epoxypropoxycarbostyril compound of the formula (IIa).

The reaction between a 2-hydroxy-3-halopropoxycarbostyril of the formula (IIb) and an amine of the formula (III) can be advantageously carried out in the presence of a base, for example, sodium hydroxide, potassium hydroxide, sodium carbonate, potassium carbonate and the like, preferably sodium carbonate or potassium carbonate, but the reaction can be carried out in the absence of such base.

The reaction can be carried out at a temperature of about 0° to about 100° C., preferably 20° to 80° C., in the absence of solvents, but advantageously carried out in the presence of solvents, e.g., alcohols such as methanol, ethanol, propanol, isopropanol and the like, aromatic hydrocarbons such as benzene, toluene, xylene and the like, water, etc., preferably alsohols such as methanol, ethanol, iropropanol and the like.

In the above reaction, the amine of the formula (III) is used in a molar excess, preferably 3 to 8 mols, per mol of the 2-hydroxy-3-halopropoxycarbostyril compound of the formula (IIb).

The reaction between a mixture of the carbostyril compounds of the formulae (IIa) and (IIb) and an amine compound of the formula (III) can be carried out in the presence or absence of the base set forth above at a temperature of about 0° C. to about 100° C., preferably 50° to 80° C. The type of solvents and the amount of the amine of the formula (III) which can be used in this reaction are the same as those set forth above for the reaction of the compound of the formula (IIa) or (IIb) with the amine of the formula (III).

The time required for completing the reaction of the carbostyril compound of the formula (IIa), (IIb) or a mixture thereof with an amine varies depending upon the temperature used, but is generally about 0.5 to about 30 hours, more generally, 2 to 14 hours.

The starting materials of the formula (II) are novel compounds and can be derived from corresponding 5,8-dihydroxycarbostyril compounds of the formula (IV) via various routes, as illustrated by Reaction Scheme 1 below.

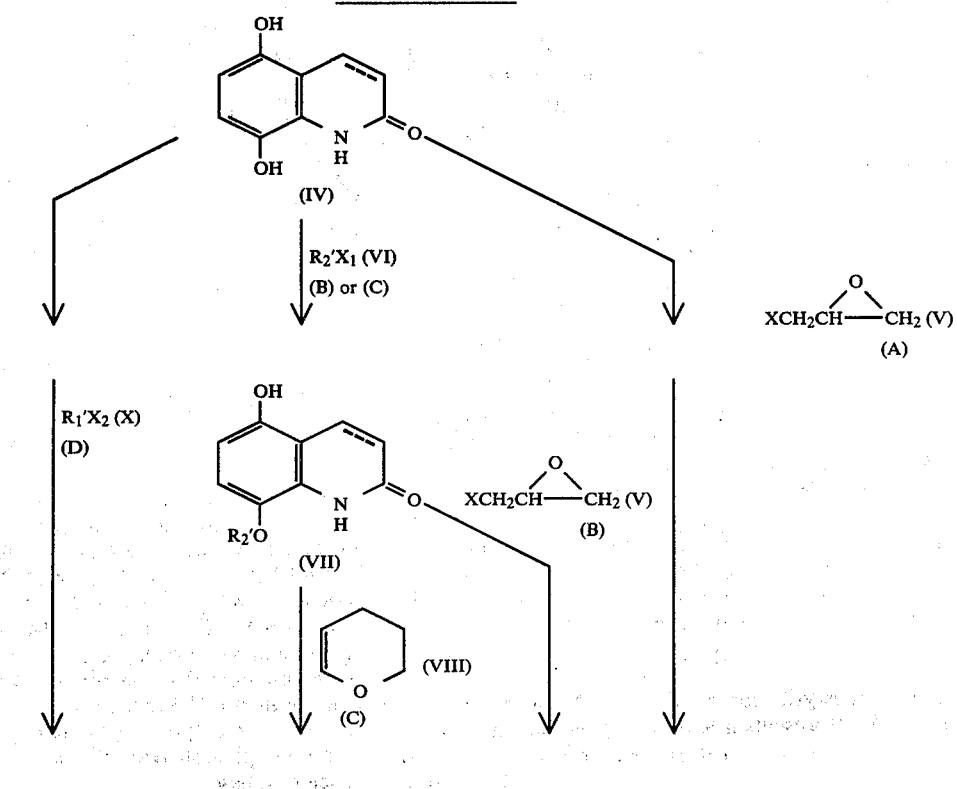

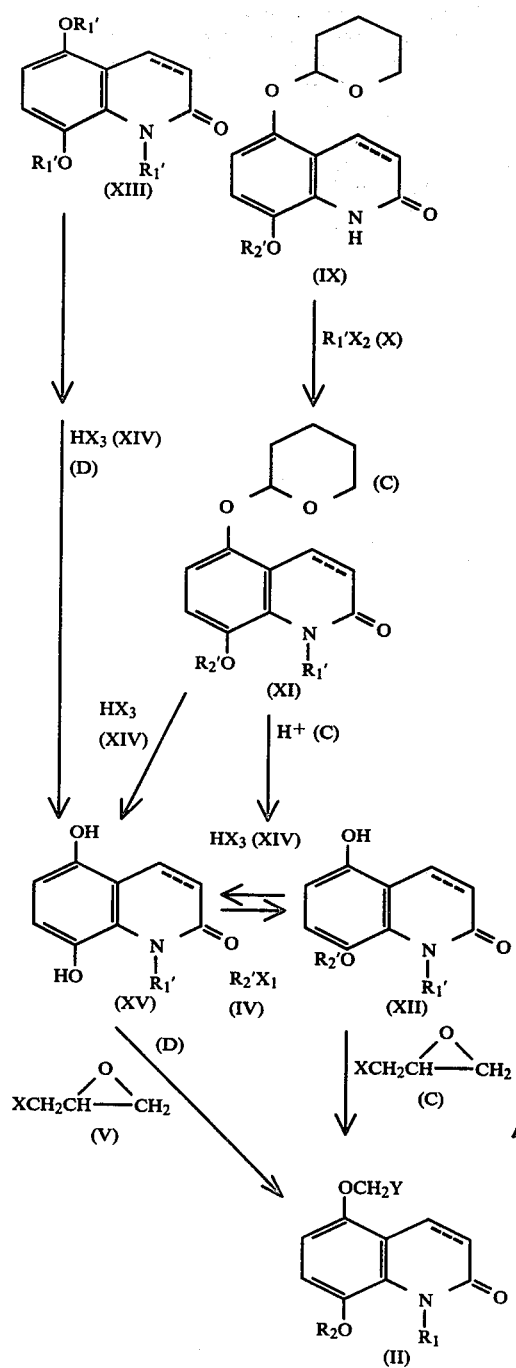
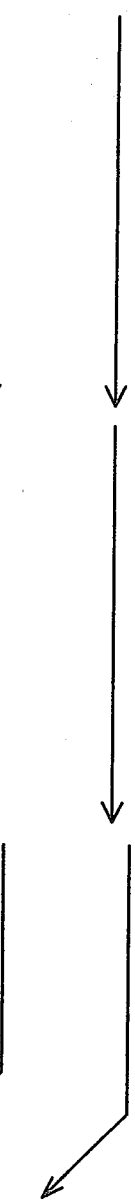

Representative procedures for the preparation of the starting materials of the formula (II) are as follows:

Method A

The carbostyril compounds of the formula (II) wherein $R_1$ and $R_2$ both represent hydrogen atoms can be prepared by reacting a known dihydroxycarbostyril compound of the formula (IV) with an epihalohydrin of the formula (V) in the presence of a base.

Method B

The carbostyril compounds of the formula (II) wherein $R_1$ represents a hydrogen atom and $R_2$ represents $R_2'$ which represents a group as defined by $R_2$ except for a hydrogen atom, can be prepared by reacting a known compound of the formula (IV) with a halide of the formula $R_2'X_1$ wherein $R_2'$ is as defined above and $X_1$ represents a halogen atom, in the presence of a base to produce a hydroxycarbostyril compound of the formula (VII) and then reacting the thus obtained hydroxycarbostyril compound of the formula (VII) with an epihalohydrin of the formula (V) in the presence of a base.

Method C

The carbostyril compounds of the formula (II) wherein $R_1$ represents $R_1'$ which represents a group as defined by $R_1$ except for a hydrogen atom and $R_2$ represents $R_2'$ which is as defined above, can be prepared by reacting a compound of the formula (VII) with a 2,3-dihydropyran of the formula (VIII) to produce a tetrahydropyranyl compound of the formula (IX) wherein the hydroxyl group at the 5-position is protected with a tetrahydropyranyl group, reacting the thus obtained compound of the formula (IX) with a halide of the formula (X) [$R_1'X_2$] in the presence of a base to produce a carbostyril compound of the formula (XI), hydrolyzing the compound of the formula (XI) to produce a corresponding hydroxycarbostyril compound of the formula (XII) and reacting the thus obtained hydroxycarbostyril compound of the formula (XII) with an epihalohydrin of the formula (V) in the presence of a base. Alternatively, the compound of the formula (XII) can be derived from the compound of the formula (XV).

Method D

The carbostyril compounds of the formula (II) wherein $R_1$ represents $R_1'$ which is as defined above and $R_2$ represents a hydrogen atom can be prepared by reacting a compound of the formula (IV) with a halide of the formula (X) [$R_1'X_2$] in the presence of a base to produce a carbostyril compound of the formula (XIII), hydrolyzing the compound of the formula (XIII) to produce a compound of the formula (XV) and then reacting the thus obtained compound of the formula (XV) with an epihalohydrin of the formula (V) in the presence of a base.

Alternatively, the compound of the formula (XV) can be prepared from the corresponding compound of the formula (XI) or (XII) by hydrolysis.

The carbostyril derivatives represented by the formula (II) include the compounds of the formulae (IIa), (IIb), (IIc) and (IId), as illustrated in Reaction Scheme 2 below, and the compounds can be converted interchangeably as shown by arrow lines.

The processes for preparing the starting compound of the formula (II) of the present invention are further illustrated hereinafter in greater detail.

The reaction between the compound of the formula (IV), (VII), (XII) or (XV) and an epihalohydrin of the formula (V) can be carried out in the presence of a base at a temperature of about 0° to about 150° C., preferably 50° to 100° C., in the absence or, preferably, in the presence of a solvent.

Suitable examples of bases which can be used in the above reaction are inorganic bases, for example, alkali metal hydroxides such as sodium hydroxide, potassium hydroxide and the like, alkali metal carbonates such as sodium carbonate, potassium carbonate and the like, alkali metals such as sodium, potassium and the like, or organic bases such as pyridine, piperidine, piperazine and the like.

Suitable examples of solvents which can be used in the above reaction are lower alcohols such as methanol, ethanol, isopropanol and the like, ketones such as acetone, methyl ethyl ketone and the like, ethers such as diethyl ether, dioxane and the like, and aromatic hydrocarbons such as benzene, toluene, xylene and the like, preferably methanol and ethanol.

The epihalohydrin of the formula (V) can be epichlorohydrin, epibromohydrin or epiiodohydrin and can be used in an amount of about 1 to about 3 mols, preferably 1 to 1.5 mols, per mol of the compound of the formula (IV) or (XV) and in an approximately equimolar amount to a molar excess amount, preferably 5 to 10 mols, per mol of the compound of the formula (VII) or (XII).

In the above reaction, the hydroxyl group attached to the 5-position of the compounds of the formulae (IV), (VII), (XII) and (XV) is converted into a (2,3-epoxy)-propoxy group or a 3-halo-2-hydroxypropoxy group and the resulting reaction product is usually a mixture of corresponding 5-(2,3-epoxy)propoxy compound and 5-(3-halo-2-hydroxypropoxy) compound. The mixture per se thus obtained is usually used for the subsequent reaction with an amine of the formula (III) without isolating each of the compounds, but, if desired, each of the compounds can be isolated and purified by conventional procedures, for example, by fractional crystalliza- Reaction Scheme 2

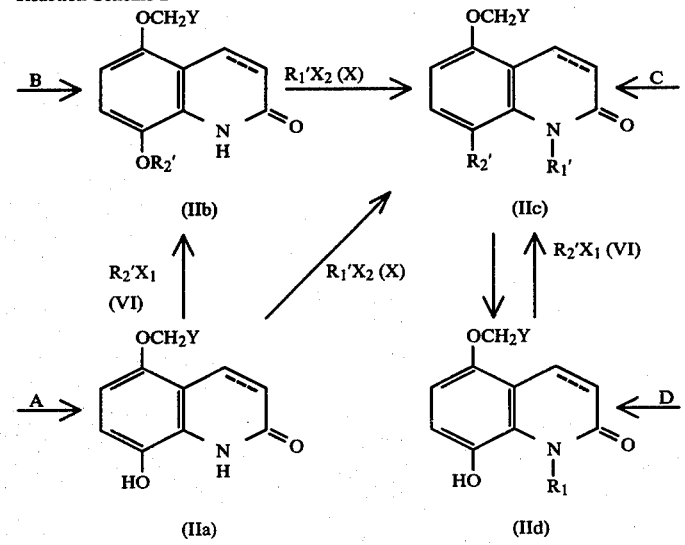

tion, column chromatography and then reacted with an amine of the formula (III).

The reaction between the compound of the formula (IIa), (IIb), (IX) or (IV) and a compound of the formula (X) [$R_1'X_2$] can be carried out by first converting the compound of the formula (IIa), (IIb), (IX) or (IV) into an alkali metal salt thereof by reacting the compound with a base such as an alkali metal or an alkali metal compound, for example, sodium hydride, potassium hydride, sodium amide, sodium, potassium and the like.

The conversion of the compound having the formula (IIa), (IIb), (IX) or (IV) into an alkali metal salt thereof can be conducted at a temperature of about 0° to about 200° C., preferably room temperature to 50° C. in a solvent, for example, aromatic solvents such as benzene, toluene, xylene and the like, n-hexane, cyclohexane, ethers such as diethyl ether, 1,2-dimethoxyethane, dioxane and the like, non-protonic polar solvents such as dimethylformamide, hexamethylphosphoric triamide, dimethyl sulfoxide and the like, preferably non-protonic polar solvents.

The alkali metal or the alkali metal compound can be used in an amount of about 1 to about 5 mols, preferably 1 to 3 mols, per mol of the compound of the formula (IIa) or (IX), and in an amount of about 2 to about 10 mols, preferably 3 to 5 mols, per mol of the compound of the formula (IIb) or (IV).

The resulting alkali metal salts of the compounds of the formulae (IIa), (IIb), (IX) and (IV) can then be reacted with a halide of the formula (X). This reaction proceeds smoothly in a solvent such as dimethylformamide, dimethyl sulfoxide and the like at room temperature (about 15° to 30° C.).

The halide (X) can be used in an amount of about 1 to about 5 mols, preferably 1 to 3 mols, per mol of the compound of the formula (IIa) or (IX), and in an amount of about 2 to about 10 mols, preferably 3 to 5 mols, per mol of the compound of the formula (IIb) or (IV).

The reaction between the compound of the formula (IIa), (IId), (IV) or (XV) and a halide of the formula (VI) [$R_2'X_1$] can be carried out in the presence of a base without using a solvent, but a solvent, e.g., ethers, such as dioxane, diethyl ether, tetrahydrofuran and the like, aromatic hydrocarbons such as benzene, toluene, xylene and the like, ketones such as acetone, methyl ethyl ketone, acetophenone and the like, dimethylformamide, acetonitrile, methanol, ethanol, etc. can be used.

Suitable examples of bases which can be used in the above reaction are inorganic bases, for example, alkali metal hydroxides such as sodium hydroxide, potassium hydroxide and the like, alkali metal carbonates such as sodium carbonate, potassium carbonate and the like, alkali metals such as sodium, potassium and the like, or organic bases such as pyridine, piperidine, piperazine and the like.

The reaction between the compound of the formula (IV) or (XV) and the halide (VI) can be conducted using about 1 mol to about 3 mols, preferably 1 to 1.5 mol, of the halide per mol of the compound of the formula (IV) or (XV) at a temperature of about 0° C. to about 100° C., preferably at 50° to 80° C.

The reaction of a compound of the formula (VII) with a 2,3-dihydropyran can be conducted in a solvent in the presence of a catalyst at a temperature of about 0° C. to a boiling point of the solvent used, preferably at room temperature to 50° C.

Suitable examples of solvents which can be used in the above reaction are aromatic solvents such as benzene, toluene, xylene and the like, n-hexane, cyclohexane, ethers such as diethyl ether, 1,2-dimethoxyethane, dioxane and the like, chloroform, dimethylformamide, hexamethylphosphoric triamide, dimethyl sulfoxide and the like.

Suitable examples of catalysts which can be used in the above reaction are inorganic acids such as sulfuric acid, hydrochloric acid, hydrobromic acid, phosphoric acid and the like, organic acids such as acetic acid, p-toluenesulfonic acid, methanesulfonic acid and the like, Lewis acids such as aluminum chloride, zinc chloride, boron trifluoride and the like, thionyl chloride, etc., in an amount of about 0.1% to about 5%, preferably 0.5% to 3%, by weight based on the weight of the compound of the formula (VII).

The removal of the tetrahydropyranyl group from the compound of the formula (IX) can be achieved by using an acid in a solvent, for example, aromatic hydrocarbons such as benzene, toluene, xylene and the like, n-hexane, cyclohexane, ethers such as diethyl ether, 1,2-dimethoxyethane, dioxane and the like, hydrated solvents for example, alcohols such as methanol, ethanol, propanol and the like, chloroform, dimethylformamide, hexamethylphosphoric triamide, dimethyl sulfoxide and the like, at a temperature of about room temperature to a boiling point of the solvent used, preferably room temperature to 50° C.

Suitable examples of acids which can be used in the removal of tetrahydropyranyl group are inorganic acids such as hydrochloric acid, sulfuric acid, phosphoric acid, hydrobromic acid and the like, and organic acids such as acetic acid, p-toluenesulfonic acid, methanesulfonic acid and the like. particularly preferred acids are weakly acidic inorganic and organic acids, for example, phosphoric acid, acetic acid, p-toluenesulfonic acid, methanesulfonic acid and the like. The amount of acids used is not critical and can be a large excess relative to the compound of the formula (IX).

The hydrolysis reaction of the compound of the formula (XI), (XII) or (XIII) can be carried out using a hydrogen halide such as hydrogen bromide, hydrogen chloride, hydrogen iodide. Generally, the hydrogen halide is used together with an appropriate solvent, in particular, with an aqueous medium, in the form of a hydrohalic acid. A particularly preferred example of the hydrogen halide is hydrogen bromide which is usually used as an aqueous solution having a concentration of about 10 to 50%, preferably 47%. The hydrogen halide can be used in an approximately 1 mol to a molar excess, preferably in a large excess amount, relative to the compound of the formula (XI), (XII) or (XIII).

The hydrolysis can be advantageously carried out under heating at a temperature of about 100° to about 150° C.

The compounds of the present invention having the formula (I) can be converted interchangeably into different types of compounds within the formula (I), as illustrated by Reaction Scheme 3 below.

Reaction Scheme 3

-continued

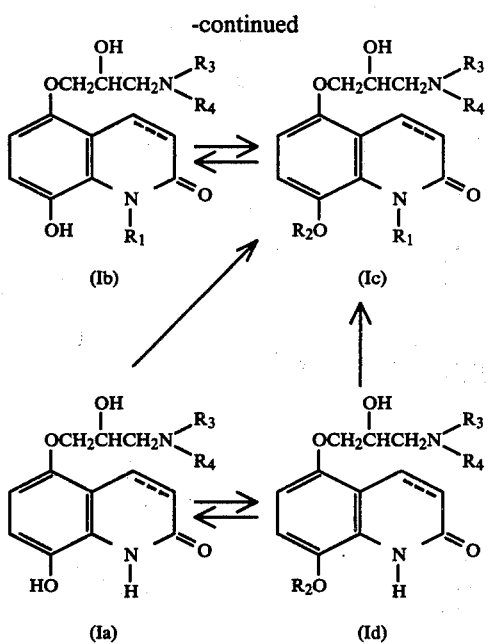

The conversion of a compound having a —OR$_2$ group at the 8-position into a corresponding compound having a —OH group at the 8-position can be achieved by catalytic reduction or hydrogenation using a reducing agent, or alkali hydrolysis or mild acid hydrolysis. Examples of R$_2$ groups which can easily be removed by the above procedures are aralkyl groups such as a benzyl group, an α-methylbenzyl group and the like, and acyl groups.

For example, the compounds of the formula (Id) and (Ic) having a benzyl group as R$_2$ can be catalytically reduced in the presence of a catalyst which is generally used for catalytic reduction, for example, Raney nickel, palladium-carbon, pallladium black, platinum oxide and the like to produce a corresponding compound of the formula (Ia) and (Ib), respectively.

The above catalytic reduction can be carried out in a solvent, for example, lower alcohols such as methanol, ethanol, isopropanol and the like, acetic acid, water, etc. The reaction conditions which can be used in the catalytic reduction are not critical and generally the reduction proceeds under atmospheric pressure at room temperature.

The thus obtained compounds of the formula (I) can be converted into their pharmaceutically acceptable acid addition salts thereof as previously described by conventional procedures which are well known in the art.

The compounds of the present invention as well as the intermediates therefor previously described can be isolated from the reaction mixture obtained in each step in conventional manners, for example, by distilling off the solvent used. If necessary, the resulting compounds can be purified by conventional procedures such as fractional crystallization, column chromatography and the like.

As is apparent to one skilled in the art, the carbostyril compounds of the formula (I) can be prepared through various routes. Representative routes which can be used are shown in Reaction Scheme 4 below.

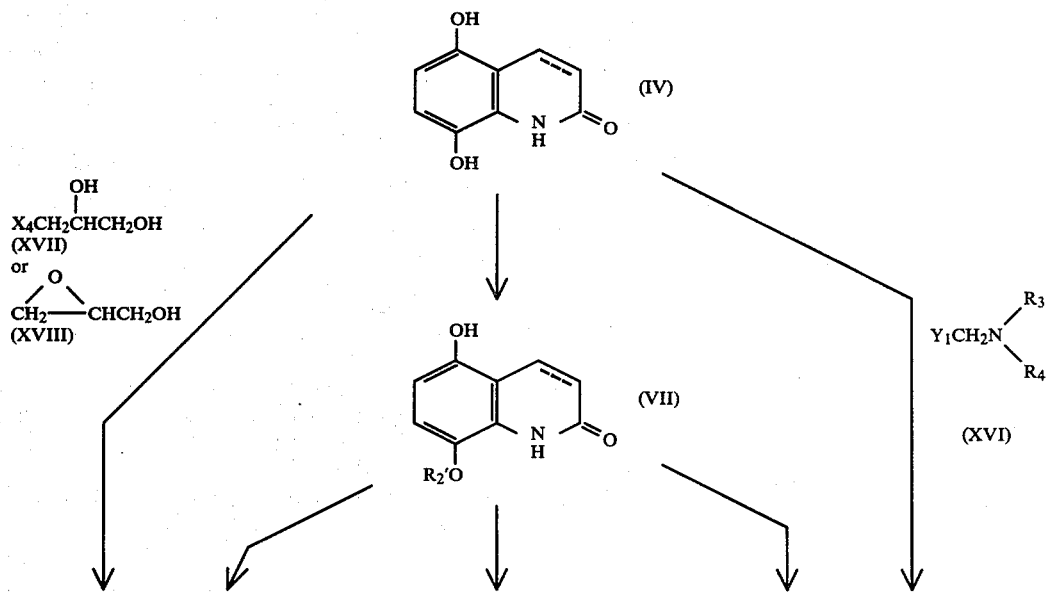

Reaction Scheme 4

-continued

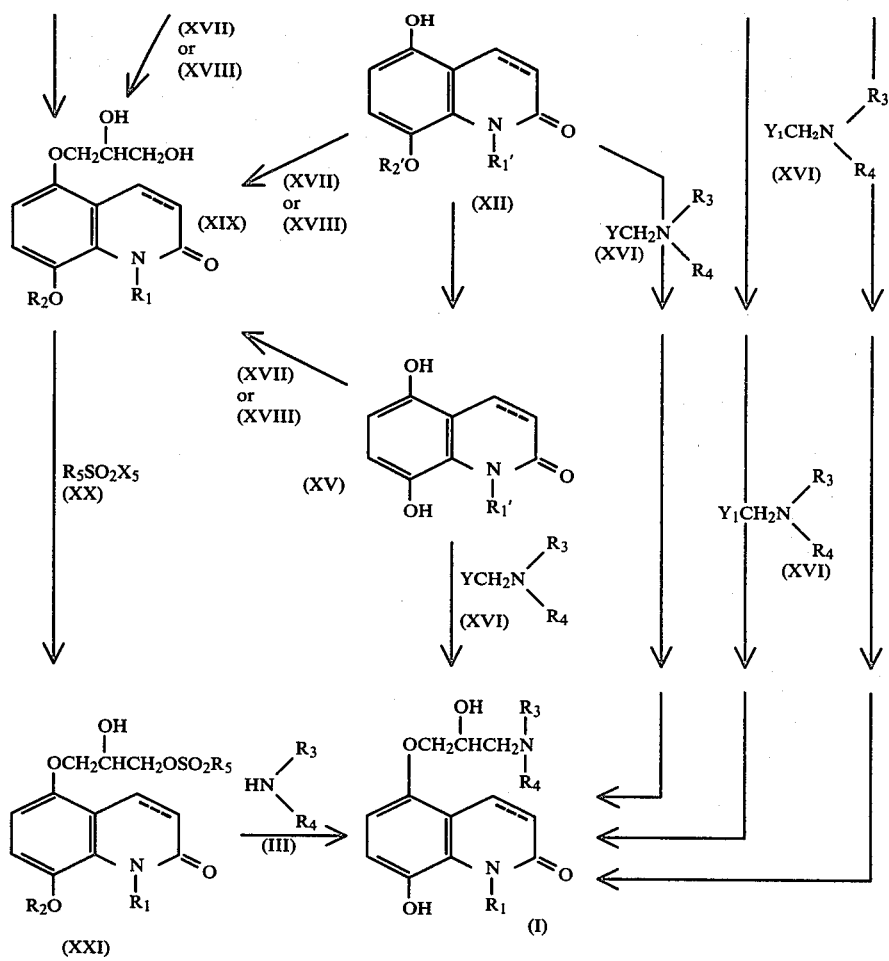

wherein $Y_1$ represents Y or $OSO_2R_5$ wherein $R_5$ represents a lower alkyl group or a phenyl group, and $X_4$ and $X_5$ each represents a halogen atom.

Further, the present invention includes, in its scope, optical isomers of the carbostyril compounds of the formula (I).

The carbostyril compounds of the present invention of the formula (I) can be easily converted into oxazolidine-carbostyril derivatives which can be produced by condensing a carbostyril compound of the formula (I) having a side chain of —OCH$_2$CH(OH)CH$_2$NH— with an aldehyde compound, and acylcarbostyril derivatives which can be produced by acylating the hydroxyl group present in the above side chain with a wide variety of acrylating agents by conventional acylating procedures. These oxazolidine- and acylcarbostyril derivatives were also found to have an excellent cardioselective β-blocking activity.

Representative compounds of the present invention having the formula (I) are:

8-benzyloxy-5-[2-hydroxy-3-(4-phenylpiperazino)-propoxy]-3,4-dihydrocarbostyril, 8-benzyloxy-5-{2-hydroxy-3-[4-(3-chlorophenyl)-piperazino]propoxy}-3,4-dihydrocarbostyril, 8-(2-propynyloxy)-5-(2-hydroxy-3-morpholino-propoxy)-3,4-dihydrocarbostyril, 8-(2-propynyloxy)-5-(3-pyrrolidino-2-hydroxy-propoxy)-3,4-dihydrocarbostyril, 8-(2-propynyloxy)-5-[2-hydroxy-3-(3-morpholino-propylamino)propoxy]-3,4-dihydrocarbostyril, 8-(2-propynyloxy)-5-(2-hydroxy-3-piperidinopropoxy)-3,4-dihydrocarbostyril, 8-(2-propynyloxy)-5-[3-(2-pyrrolidinoethylamino)-2-hydroxypropoxy]-3,4-dihydrocarbostyril, 8-(2-propynyloxy)-5-{2-hydroxy-3-[2-(N-methyl-piperazino)ethylamino]propoxy}-3,4-dihydrocarbostyril, 8-(2-propynyloxy)-5-[3-(4-piperizinobutylamino)-2-hydroxypropoxy)]-3,4-dihydrocarbostyril, 8-(2-propynyloxy)-5-[3-(2-pyrazolidinoethylamino)-2-hydroxypropoxy]-3,4-dihydrocarbostyril, 8-(2-propynyloxy)-5-[3-(N-ethylpiperazino)-2-hydroxypropoxy]-3,4-dihydrocarbostyril, 8-(2-propynyloxy)-5-[2-hydroxy-3-(2-methylmorpholino)propoxy]-3,4-dihydrocarbostyril, 8-(3-butynyloxy)-5-[2-hydroxy-3-(3-morpholino-propylamino)propoxy]-3,4-dihydrocarbostyril, 8-(2-methyl-3-butynyloxy)-5-{2-hydroxy-3-[3-(4-phenylpiperazino)ethylamino]propoxy}-3,4-dihydrocarbostyril, 8-(2-hydroxyethoxy)-5-[2-hydroxy-3-(3-morpholino-propylamino)propoxy]-3,4-dihydrocarbostyril, 8-(2-hydroxyethoxy)-5-(2-hydroxy-3-morpholino-propoxy)-3,4-dihydrocarbostyril, 8-(2-hydroxyethoxy)-5-(3-piperidino-2-hydroxy-propoxy)-3,4-dihydrocarbostyril, 8-(2-hydroxyethoxy)-5-[3-(N-phenylpiperazino)-2-hydroxypropoxy]-3,4-dihydrocarbostyril, 8-(2-hydroxyethoxy)-5-(3-pyrrolidino-2-hydroxypropoxy)-3,4-dihydrocarbostyril, 8-(3-hydroxypropoxy)-5-[3-(3-pyrrolidinopropylamino)-2-hydroxypropoxy]-3,4-dihydrocarbostyril, 8-(2-methyl-4-hydroxybutoxy)-5-[3-(N-phenylpiperazino)-2-hydroxypropoxy]-3,4-dihydrocarbostyril, 8-(2-propynyloxy)-5-[3-(4-piperizinobutylamino)-2-hydroxypropoxy]carbostyril, 8-(2-propynyloxy)-5-(2-hydroxy-3-morpholinopropoxy)carbostyril, 8-(2-propynyloxy)-5-(2-hydroxy-N-methylpiperazinopropoxy)carbostyril, 8-(2-propynyloxy)-5-[2-hydroxy-3-(3-morpholinopropylamino)propoxy]carbostyril, 8-(2-propynyloxy)-5-[2-hydroxy-3-(4-phenylpiperazino)propoxy]carbostyril, 8-(2-hydroxyethoxy)-5-[2-hydroxy-3-(3-morpholinopropylamino)propoxy]carbostyril, 8-(2-hydroxyethoxy)-5-[3-(N-phenylpiperazino)-2-hydroxypropoxy]carbostyril, 8-(2-propynyloxy)-5-{2-hydroxy-3-[4-(4-methoxyphenyl)piperazino]propoxy}-3,4-dihydrocarbostyril, 8-(2-propynyloxy)-5-{2-hydroxy-3-[4-(2-methylphenyl)piperazino]propoxy}-3,4-dihydrocarbostyril, 8-(2-propynyloxy)-5-{2-hydroxy-3-[4-(4-chlorophenyl)piperazino]propoxy}-3,4-dihydrocarbostyril, 8-(2-hydroxyethoxy)-5-{2-hydroxy-3-[4-(4-methoxyphenyl)piperazino]propoxy}-3,4-dihydrocarbostyril, 8-(2-hydroxyethoxy)-5-{2-hydroxy-3-[4-(4-chlorophenyl)piperazino]propoxy}-3,4-dihydrocarbostyril, 8-benzyloxy-5-{2-hydroxy-3-[4-(4-methoxyphenyl)piperazino]propoxy}-3,4-dihydrocarbostyril, 8-hydroxy-5-[2-hydroxy-3-(4-phenylpiperazino)propoxy]carbostyril, 8-(2-methoxyethoxy)-5-{2-hydroxy-3-[4-(4-methoxyphenyl)piperazino]propoxy}-3,4-dihydrocarbostyril, 8-acetoxy-5-{2-hydroxy-3-[4-(3-chlorophenyl)piperazino]propoxy}-3,4-dihydrocarbostyril, 8-(2-propynyloxy)-5-[2-hydroxy-3-(4-phenylpiperazino)propoxy]-3,4-dihydrocarbostyril, and the like.

The present invention is further illustrated by the following Examples, but these Examples are given for illustrative purposes only and not to be construed as limiting the present invention. Unless otherwise indicated, all parts, percents, ratios and the like are by weight.

REFERENCE EXAMPLE 1

21.6 g of 5,8-dihydroxy-3,4-dihydrocarbostyril and 19.9 g of potassium carbonate were added to a mixture comprising 480 ml of acetone and 120 ml of water, and the resulting mixture was stirred while refluxing for 30 minutes. 76 g of 2-methoxyethyl bromide was then added thereto followed by stirring while refluxing for 8 hours. The solvent was evaporated, and water was added to the residue. The mixture was extracted with diethyl ether. The aqueous layer was rendered acidic with hydrochloric acid and then extracted with chloroform. The chloroform layer was dried over anhydrous magnesium sulfate, and the chloroform evaporated to obtain 15 g of 5-hydroxy-8-(2-methoxyethoxy)-3,4-dihydrocarbostyril as a black oily substance.

REFERENCE EXAMPLE 2

0.7 g of 8-hydroxy-5-(3-t-butylamino-2-hydroxypropoxy)-3,4-dihydrocarbostyril was suspended in 20 ml of acetone, and 3.0 ml of 1 N NaOH was added to the suspension to form a homogeneous solution. 0.2 g of acetyl chloride dissolved in a small amount of acetone was added dropwise to the solution under ice-cooling and stirring. After the mixture was allowed to stand under ice-cooling for 30 minutes, 2 ml of 1 N hydrochloric acid was added to the mixture, and the solvent evaporated under reduced pressure. The residue was purified by silica gel column chromatography using chloroform:methanol (8:1 by volume) as an eluent. The solvent was evaporated, and the residue was recrystallized from methanol-diethyl ether to obtain 0.4 g of 8-acetoxy-5-(3-t-butylamino-2-hydroxypropoxy)-3,4-dihydrocarbostyril hydrochloride as colorless flake-like crystals having a melting point of 247°–248° C. (with decomposition).

REFERENCE EXAMPLE 3

2 liters of acetone and 500 ml of water were added to 150 g of 5,8-dihydroxy-3,4-dihydrocarbostyril, and 138 g of potassium carbonate and 150 g of 2-propynyl bromide were further added thereto. The resulting mixture was heated while refluxing for 3 hours on a water bath. After completion of the reaction, the acetone and the 2-propynyl bromide were evaporated under reduced pressure, and the residue was made acidic with concentrated hydrochloric acid. The mixture was extracted with chloroform, and the chloroform layer was washed with water and dried over anhydrous sodium sulfate. The chloroform was evaporated under reduced pressure, and the residual crystals were recrystallized from isopropanol-diethyl ether to obtain 110 g of 8-(2-propynyloxy)-5-hydroxy-3,4-dihydrocarbostyril having a melting point of 141°–142° C.

REFERENCE EXAMPLE 4

To 78 g of 8-(2-propynyloxy)-5-hydroxy-3,4-dihydrocarbostyril were added 102 g of epichlorohydrin, 60 g of potassium carbonate and 600 ml of methanol, and the resulting mixture was heated while refluxing for 2.5 hours on a water bath. After completion of the reaction, the methanol was evaporated, and water was added to the residue followed by extracting with chloroform. The chloroform layer was washed with water and dried over anhydrous sodium sulfate. The chloroform was evaporated under reduced pressure, and the residual crystals were recrystallized from isopropanol to obtain 67 g of 8-(2-propynyloxy)-5-(2,3-epoxypropoxy)-3,4-dihydrocarbostyril having a melting point of 142°–143.5° C.

EXAMPLE 1

1.0 g of 8-(2-propynyloxy)-5-(3-chloro-2-hydroxypropoxy)-3,4-dihydrocarbostyril was dissolved in 20 ml of methanol. 0.7 g of anhydrous potassium carbonate and 1.7 g of morpholine were then added to the solution followed by stirring while refluxing for 4 hours. After completion of the reaction, the methanol and the unreacted morpholine were evaporated under reduced pressure, and the residual oil was converted into a hydrochloride with an aqueous hydrochloric acid, and washed with chloroform. The aqueous layer was separated, made alkaline with sodium hydroxide and extracted with chloroform. The chloroform layer was washed with water and dried over anhydrous sodium sulfate. The chloroform was evaporated under reduced pressure, and the residue was converted into a hydrochloride with ehtanolhydrochloric acid. Recrystallization from water-ethanol gave 0.8 g of 8-(2-propynyloxy)-5-(2-hydroxy-3-morpholinopropoxy)-3,4-dihydrocarbostyril hydrochloride having a melting point of 234.5°–235° C.

EXAMPLE 2

2 g of 8-(2-propynyloxy)-5-(2,3-epoxypropoxy)-3,4-dihydrocarbostyril was dissolved in 30 ml of methanol, and 2.6 g of pyrrolidine was added thereto, followed by allowing the mixture to stand at 10° to 15° C. for 12 hours. After the reaction, the methanol and the unreacted pyrrolidine were evaporated under reduced pressure. The residual oil was converted into a hydrochloride with hydrochloric acid-ethanol. Recrystallization from methanol gave 0.9 g of 8-(2-propynyloxy)-5-(3-pyrrolidino-2-hydroxypropoxy)-3,4-dihydrocarbostyril hydrochloride having a melting point of 225°–226° C.

EXAMPLES 3 TO 21

In the same manner as described in Example 2, the following compounds were prepared:

| Example No. | Bonding at 3,4-Position of Carbostyril Structure | $R_1$ | $R_2$ | $-N\begin{smallmatrix}R_3\\R_4\end{smallmatrix}$ | HA | Melting Point (°C.) |
|---|---|---|---|---|---|---|
| 3 | single bond | H | $-CH_2-$phenyl | $-N$(piperazinyl)$-$phenyl | HCl | 227–228 |
| 4 | single bond | H | $-CH_2-$phenyl | $-N$(piperazinyl)$-$(3-Cl-phenyl) | HCl | 215–216.5 |
| 5 | single bond | H | $-CH_2-$phenyl | $-N$(piperazinyl)$-$(4-$OCH_3$-phenyl) | HCl | 223–225 |
| 6 | single bond | H | $-CH_2-$phenyl | $-N$(2-methylpiperazinyl)$-$(4-Cl-phenyl) | HCl | 180–182 |
| 7 | single bond | H | H | $-N$(2-methylpiperazinyl)$-$(4-Cl-phenyl) | HCl | 279–281 |
| 8 | single bond | H | H | $-N$(piperazinyl)$-$phenyl | HCl | 275–277 |
| 9 | single bond | H | H | $-N$(piperazinyl)$-$(4-$OCH_3$-phenyl) | HCl | 268–270 |
| 10 | single bond | H | H | $-N$(piperazinyl)$-$(3-Cl-phenyl) | HCl | 273–275 |

-continued

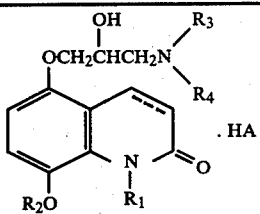

| Example No. | Bonding at 3,4-Position of Carbostyril Structure | $R_1$ | $R_2$ | $-N\begin{matrix}R_3\\R_4\end{matrix}$ | HA | Melting Point (°C.) |
|---|---|---|---|---|---|---|
| 11 | double bond | H | $-CH_2-\text{Ph}$ | $-N\underset{\phantom{x}}{\diagup\diagdown}N-\text{Ph}$ | HCl | 212–213 |
| 12 | double bond | H | H | $-N\underset{\phantom{x}}{\diagup\diagdown}N-\text{Ph-Cl}$ (with $CH_3$ on ring) | HCl | 268.5–270 |
| 13 | single bond | H | $-CH_2C\equiv CH$ | $-NHCH_2CH_2CH_2N\underset{\phantom{x}}{\diagup\diagdown}O$ | 2HCl · ½H₂O | 227–228 (decomp.) |
| 14 | single bond | H | $-CH_2C\equiv CH$ | $-N\underset{\phantom{x}}{\diagup\diagdown}$ | HCl | 206–207 |
| 15 | single bond | H | $-CH_2C\equiv CH$ | $-N\underset{\phantom{x}}{\diagup\diagdown}N-\text{Ph}$ | HCl | 225–226 (decomp.) |
| 16 | single bond | H | $-CH_2C\equiv CH$ | $-N\underset{\phantom{x}}{\diagup\diagdown}N-\text{Ph}(CH_3O\text{-})$ | HCl | 205–206 |
| 17 | single bond | H | $-CH_2C\equiv CH$ | $-N\underset{\phantom{x}}{\diagup\diagdown}N-\text{Ph}(CH_3\text{-})$ | HCl | 202–203 |
| 18 | single bond | H | $-CH_2C\equiv CH$ | $-N\underset{\phantom{x}}{\diagup\diagdown}N-\text{Ph}-OCH_3$ | HCl | 224–225 |
| 19 | double bond | H | $-CH_2C\equiv CH$ | $-NHCH_2CH_2CH_2N\underset{\phantom{x}}{\diagup\diagdown}O$ | HCl | 214–215 (decomp.) |
| 20 | double bond | H | $-CH_2C\equiv CH$ | $-N\underset{\phantom{x}}{\diagup\diagdown}N-\text{Ph}-OCH_3$ | HCl | 212–213.5 |
| 21 | single bond | H | $-CH_2C\equiv CCH_2CH(CH_3)_2$ | $-N\underset{\phantom{x}}{\diagup\diagdown}O$ | Free | 93–95 |

REFERENCE EXAMPLE 5

The β-adrenergic blocking activity of the compounds of this invention was determined as follows: Male hybrid adult dogs, weighing 10 to 16 kg, were anesthesized with sodium pentobarbital administered intravenously at a level of 30 mg/kg of body weight, and a cannula was inserted into the trachea of each of the anesthesized dogs. In order to avoid blood coagulation, heparin was administered intravenously at a level of 1000 units and thereafter a cannula was inserted into the right femoral artery. The experiments were conducted under artificial respiration at a rate of 20 ml/kg, 18 r.p.m.

The blood pressure was determined using a pressure transducer (MPU-0.5 Type, tradename of Nippon Koden Co., Japan) and the heart rate (HR) was determined from the pulse wave of blood pressure using an instantaneous heart rate tachometer (2130 Type, tradename of Sanei Sokki Co., Japan). The air-way resistance (AR) was determined according to the Könzett-Rössler Method (Könzett H. & Rössler R., "Versuchsanordnug zu Untersuchungen an der Bronchial Moskolatur" Arch. Exp. Path., Pharmak, 195, 71–74, 27–40 (1940) using a low-pressure type pressure transducer (LPU-0.1, tradename of Nippon Koden Co., Japan).

The above parameters were continuously recorded on a polygraph (8S 28 Type, tradename of Sanei Sokki Co., Japan). During the experiment, gallamine was administered intravenously at a dosage of 3 mg/kg at one-hour intervals to avoid fluctuation of air-way resistance.

The β-adrenergic blocking activity of each of the test compounds was evaluated in terms of antagonism (Inhibition %) to the depression at the diastolic blood pressure (dBP) and to the increase in the heart rate induced by the intravenous administration of isoprenaline (1 μg/kg) and in terms of antagonism (Inhibition %) to the depression by isoprenaline in increase of air-way resistance which was induced by intravenous administration of histamine (5 μg/kg). In this case, histamine was administered 45 seconds after the administration of isoprenaline.

The β-adrenergic blocking activity of the test compounds was determined 10 minutes after the intravenous administration of the test compounds at a level of 300 μg/kg and the results obtained are shown in Table 1 below, where Proctolol Table 1

(CH₃CNH—⟨Ph⟩—OCH₂CHCH₂NHCH(CH₃)₂, OH) and Atenolol (H₂NCCH₂—⟨Ph⟩—OCH₂CHCH₂NHCH(CH₃)₂, OH) were used as controls.

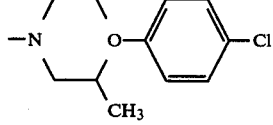

| Sample No. | R₁ | R₂ | R₃, R₄ (–NR₃R₄) | HA | Inhibition (%) HR*¹ | dBP*² | Ar*³ |
|---|---|---|---|---|---|---|---|
| 1 | H | —OCH₂C≡CH | —NHCH₂CH₂CH₂—N⟨morpholine⟩ | HCl | 58.5 | 59.5 | 35.4 |
| 2 | H | —OCH₂—⟨Ph⟩ | —N⟨morpholine-CH₃⟩—O—⟨Ph⟩—Cl | HCl | 25.7 | 20.6 | 15.5 |
| 3 | H | H | —N⟨piperazine⟩N—⟨Ph⟩—OCH₃ | HCl | 71.6 | 66.8 | 42.7 |
| 4 | H | —OCH₂C≡CH | —N⟨piperidine⟩ | HCl | 63.5 | 44.2 | 28.7 |
| 5 | H | —OCH₂C≡CH | —NHCH₂CH₂CH₂N⟨morpholine⟩ | HCl | 58.5 | 59.5 | 35.4 |

Table 1-continued

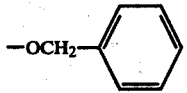

(CH₃CNH—⟨benzene⟩—OCH₂CHCH₂NHCH(CH₃)₂ with OH) and Atenolol (H₂NCCH₂—⟨benzene⟩—OCH₂CHCH₂NHCH(CH₃)₂ with OH) were used as controls.

General structure:

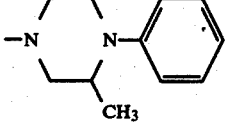

| Sample No. | R₁ | R₂ | R₃, R₄ | HA | Inhibition (%) HR*1 | dBP*2 | Ar*3 |
|---|---|---|---|---|---|---|---|
| 6 | H | —OCH₂—⟨phenyl⟩ | —N(piperazine)-N-⟨phenyl with CH₃⟩ | HCl | 25.7 | 20.6 | 15.5 |

Prior Art Compounds

| | R₁ | R₂ | R₃, R₄ | HA | HR*1 | dBP*2 | Ar*3 |
|---|---|---|---|---|---|---|---|
| 1 | H | OH | —NH—C(CH₃)₃ | HCl | 100 | 100 | 100 |
| 2 | H | —OCH₃ | —NH—C(CH₃)₃ | HCl | 82.1 | 83.7 | 80.2 |
| 3 | H | —OCH₂—⟨phenyl⟩ | —NH—C(CH₃)₃ | HCl | 71.3 | 10.2 | 67.8 |
| 1 | H | H | —NH—C(CH₃)₃ | HCl | 100 | 100 | 100 |
| 2 | H | H | —NHCH₂CH₂—⟨phenyl with OCH₃, OCH₃⟩ | HCl | 87.2 | 65.6 | 79.1 |
| 3 | | Proctolol | | | 44.6 | 1.7 | 36.2 |
| 4 | | Atenolol | | | 52.3 | 26.9 | 9.8 |

*1 HR = Heart Rate
*2 dBP = Diastolic Blood Pressure
*3 AR = Air-Way Resistance

Further, the acute toxicity of the compounds of the present invention having the formula (I) was determined by intravenous administration (i.v.) and oral administration (p.o.) in 5 to 6 group of rats (dd, strain; body weight, 18 to 22 g; 10 rats in each group) which have been fasted for 12 hours prior to the test. A typical compound of the present invention of the formula (I), 5-[3-(4-phenylpiperazino)-2-hydroxypropoxy]-8-benzyloxy-3,4-dihydrocarbostyril hydrochloride, was found to have the following $LD_{50}$ (50% lethal dose):

| | i.v. | p.o. |
|---|---|---|
| Rats (Male) | 160 mg/kg | 1550 mg/kg |
| Rats (Female) | 145 mg/kg | 1450 mg/kg |

The other compounds of the formula (I) were also found to have low toxicity, i.e., higher than about 130 mg/kg (i.v.) and higher than about 1200 mg/kg (p.o.).

The compounds of the present invention can be administered at a dosage level of from about 40 ug to about 2 mg/kg/day by oral administration. Typical examples of suitable formulations are given below, but it is to be noted that other dosage forms can also be prepared using other compounds of this invention as well as other excipients which are well known to one skilled in the art, according to the well-established pharmaceutical techniques.

FORMULATION 1

Tablets each containing the following components were prepared from the following components:

| Components | Amount |
| --- | --- |
| 8-Hydroxy-5-{3-[4-(3-chlorophenyl)-piperazino]-2-hydroxypropoxy}-3,4-dihydrocarbostyril Hydrochloride | 5 mg |
| Corn Starch | 142 mg |
| Magnesium Stearate | 18 mg |
| Lactose | 45 mg |
| Total | 200 mg |

FORMULATION 2

Tablets each containing the following components were prepared from the following components:

| Components | Amount |
| --- | --- |
| 8-Hydroxy-5-{3-[4-(3-chlorophenyl)-piperazino]-2-hydroxypropoxy}-3,4-dihydrocarbostyril Hydrochloride | 10 mg |
| Corn Starch | 140 mg |
| Magnesium Stearate | 18 mg |
| Lactose | 42 mg |
| Total | 200 mg |

What is claimed is:

1. A carbostyril compound represented by the formula (I):

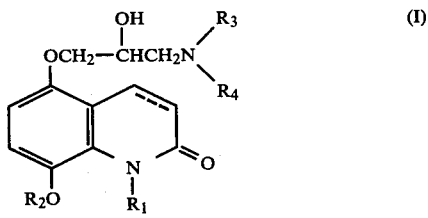

wherein $R_1$ represents a hydrogen atom, $R_2$ represents a hydrogen atom, a phenylalkyl group selected from the group consisting of monophenylalkyl and diphenylalkyl groups having a straight or branched chain alkyl group having 1 to 6 carbon atoms in the alkyl moiety, an alkoxyalkyl group having a straight or branched chain alkoxy group of 1 to 6 carbon atoms in the alkoxy moiety thereof and a straight or branched chain alkylene group of 1 to 6 carbon atoms in the alkyl moiety thereof, a mono hydroxyalkyl group having a straight or branched chain alkyl group of 1 to 6 carbon atoms, an alkylcarbonyl group having a straight or branched chain alkyl group of 1 to 6 carbon atoms in the alkyl moiety thereof, or a straight or branched chain alkynyl group having 2 to 7 carbon atoms, $R_3$ represents a hydrogen atom, and $R_4$ represents a pyrrolidinoalkyl group having a straight or branched alkylene group of 1 to 6 carbon atoms, a piperazinoalkyl group having a straight or branched alkylene group of 1 to 6 carbon atoms, or a morpholinoalkyl group having a straight or branched alkylene group of 1 to 6 carbon atoms, or $R_3$ and $R_4$ can form, when taken together with the nitrogen atom to which they are attached, a piperidino group, a morpholino group, a pyrrolidino group or a piperazino group, said phenylalkyl, pyrrolidinoalkyl, piperazinoalkyl, morpholinoalkyl, piperidino, morpholino, pyrrolidino or piperazino group optionally containing 1 to 3 substituents selected from the class contsisting of an alkyl group having 1 to 4 carbon atoms, an alkoxy group having 1 to 4 carbon atoms, a halogen atom, an alkylenedioxy group of 1 to 2 carbon atoms, a carbamoyl group and a phenyl group, the 3,4-bond of the carbostyril nucleus represents a single bond, and the pharmaceutically acceptable acid additional salts thereof.

2. 8-Benzyloxy-5-[2-hydroxy-3-(4-phenylpiperazino)-propoxy]-3,4-dihydrocarbostyril according to claim 1.

3. 8-Benzyloxy-5-{2-hydroxy-3-[4-(3-chlorophenyl)-piperazino]propoxy}-3,4-dihydrocarbostyril according to claim 1.

4. 8-(2-Propynyloxy)-5-(2-hydroxy-3-morpholinopropoxy)3,4-dihydrocarbostyril according to claim 1.

5. 8-(2-Propynyloxy)-5-(3-pyrrolidino-2-hydroxypropoxy)-3,4-dihydrocarbostyril according to claim 1.

6. 8-(2-Propynyloxy)-5-[2-hydroxy-3-(3-morpholinopropylamino)propoxy]-3,4-dihydrocarbostyril according to claim 1.

7. 8-(2-Propynyloxy)-5-(2-hydroxy-3-piperidinopropoxy)-3,4-dihydrocarbostyril according to claim 1.

8. 8-(2-Propynyloxy)-5-[2-hydroxy-3-(4-phenylpiperazino)propoxy]-3,4-dihydrocarbostyril according to claim 1.

* * * * *

UNITED STATES PATENT AND TRADEMARK OFFICE
CERTIFICATE OF CORRECTION

PATENT NO. : 4,210,753
DATED : July 1, 1980
INVENTOR(S) : TOMINAGA ET AL

It is certified that error appears in the above-identified patent and that said Letters Patent are hereby corrected as shown below:

In Table 1 in the Specification, Columns 23-24, in Sample No. 3, in the second column to the right of the sample number, designated $R_2$, delete "H" and substitute therefor -- -OH --.

Signed and Sealed this

Third Day of March 1981

[SEAL]

Attest:

RENE D. TEGTMEYER

Attesting Officer

Acting Commissioner of Patents and Trademarks